United States Patent
Knoblauch et al.

(10) Patent No.: US 7,902,331 B2
(45) Date of Patent: Mar. 8, 2011

(54) FORISOMES, METHOD FOR THEIR ISOLATION, AND THEIR USE AS A MOLECULAR WORKING MACHINE

(75) Inventors: Michael Knoblauch, Butzbach (DE); Dirk Prüfer, Köln (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 2278 days.

(21) Appl. No.: 10/605,104

(22) Filed: Sep. 9, 2003

(65) Prior Publication Data
US 2009/0012262 A1 Jan. 8, 2009

(30) Foreign Application Priority Data

Sep. 9, 2002 (DE) .................................. 102 41 681

(51) Int. Cl.
*C07K 14/415* (2006.01)
*C07K 7/08* (2006.01)
*A61K 36/48* (2006.01)

(52) U.S. Cl. ......... 530/328; 530/329; 530/370; 424/757; 435/4

(58) Field of Classification Search .................. None
See application file for complete search history.

(56) References Cited

OTHER PUBLICATIONS

Knoblauch, M., et al. 2003 Nature Materials 2: 600-603.*
Michael Knoblauch et al., Reversible Calcium-Regulated Stopcoks in Legume Sieve Tubes; The Plant Cell, May 13, 2001 (5): 1221-1230, American Society of Plant Biologists.
H.-Dietmar Behnke, Nondispersive Protein Bodies in Sieve Elements: A Survey and Review of Their Origin, Distribution and Taxonomic Significance, IAWA Bulletin vol. 12 (2) 1991, pp. 143-175.

* cited by examiner

*Primary Examiner* — Manjunath N Rao
*Assistant Examiner* — Marsha M Tsay
(74) *Attorney, Agent, or Firm* — Gudrun E. Huckett

(57) ABSTRACT

A protein body derivable from Fabaceae has a reversible, anisotropic contractability such that the protein body becomes thicker perpendicular to a longitudinal axis of the protein body and shorter along the longitudinal axis of the protein body when increasing a calcium ion concentration in a medium surrounding the protein body past a threshold value of 30 nM. The protein body becomes thinner perpendicular to the longitudinal axis and longer along the longitudinal axis when decreasing the calcium ion concentration below the threshold value of 30 nM. Also, the protein body becomes thicker in the direction perpendicular to the longitudinal axis when increasing a pH value of a medium surrounding the protein body to a value above 9.5 without becoming shorter along the longitudinal axis. The protein body becomes thinner in the direction perpendicular to the longitudinal axis without becoming longer decreasing the pH value below 9.5.

12 Claims, 7 Drawing Sheets

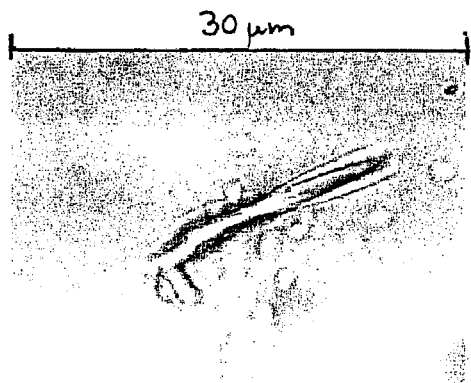
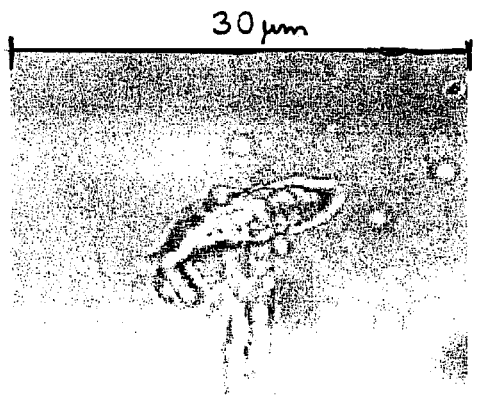
Fig. 1A    Fig. 1B
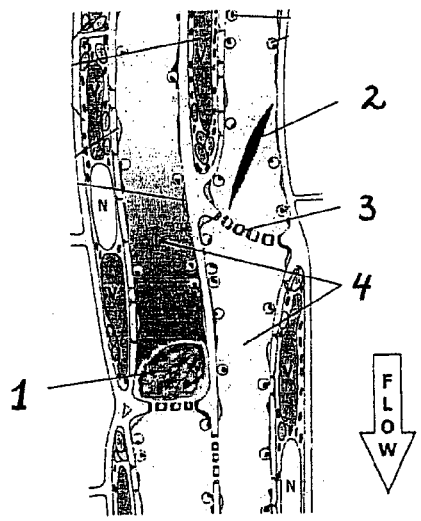
Fig. 2

Fig. 7A

Fig. 7B object    forisome object    forisome contact     forisome     conductor contact     forisome     conductor

FORISOMES, METHOD FOR THEIR ISOLATION, AND THEIR USE AS A MOLECULAR WORKING MACHINE

BACKGROUND OF INVENTION

1. Field of the Invention

The invention relates to forisomes, i.e., protein bodies which are also referred to as crystalline P-proteins, and which, according to the present knowledge in the art, are present exclusively, but ubiquitously, in plants of the legume family (Fabaceae, Papillionaceae). These protein bodies have very extraordinary, heretofore unknown, properties which enable their use as molecular working machines. Moreover, the invention relates to a method for isolating forisomes from their natural environment.

2. Description of the Related Art

The phloem of higher plants contains a system of microtubules (sieve elements) extending throughout the plant and serving for transporting photo assimilate (see FIG. 2). The sieve elements are comprised of cells that, as a whole, form a capillary system through the entire plant, i.e., the aforementioned phloem. This is a micro fluidic system having an inner pressure of up to 3.5 MPa and maximum flow velocities up to 3 cm/min$^{-1}$.

Crystalline P-proteins are specific ingredient bodies of the sieve elements of the legume family of plants (Fabaceae). They were first observed in plant cuts and described as usually elongate compact structures up to a length of 30 µm with a highly ordered ("crystalloid") ultra structure. Their function, however, remained unclear for more than a century after their discovery (Behnke, H. D., Nondispersive protein bodies in sieve elements: a survey and review of their origin, distribution and taxonomic significance; IAWA Bull, 12, 143-175 (1991)). In the meantime, it was found that they deform suddenly upon the occurrence of drastic changes of the hydrostatic pressure in the interior of the sieve elements. The proteins convert from an ordered "crystalloid" state (spindle shaped) (see reference numeral 2 in FIG. 2) into a "disperse" conformation that ultra-structurally appears to be less ordered (see reference numeral 1 in FIG. 2; in this Figure reference numeral 3 describes a sieve plate and reference numeral 4 the sieve elements). The dispersed form has a rounded configuration and forms plugs in the sieve tubes and reduces thus the further flow of the liquid rich with photo assimilates within the tube system. However, in this connection the protein bodies apparently do not lose their internal organization because they are still capable of spontaneously converting back to the ordered "crystalloid" state. A work group of the inventors was able to demonstrate that the observed confirmation changes in situ can be sufficiently explained by the dependency of the confirmation of crystalline P-proteins from certain divalent cations (Knoblauch, M., Peters, W. S., Ehlers, K. and van bel, A. J. E.; Reversible calcium-regulated stopcocks in legume sieve tubes. Plant Cell 13, 1221-1230 (2001)). The "crystalloid" state is present at Ca$^{++}$ concentrations of significantly less than 1 µM, as can be adjusted with chelating agents, while concentrations in the micromolar range results in transformation into the "dispersed" conformation. With respect to the biological function of the protein bodies, they were given the name "forisomes", derived from "foris" (Latin for door) and "soma" (Greek for body).

SUMMARY OF INVENTION

It is an object of the present invention to isolate the P-proteins, which have been previously observed only in situ, to characterize them, to provide a reproducible method for their preparation, and to check whether they are useful and, optionally, for which purpose they are useful.

As a solution to this object, the inventors for the first time were successful in isolating forisomes of plants of the legume family (Fabaceae). This isolation was found to be extremely difficult. It is possible to push individual protein bodies manually out of the cell and to transfer them onto a microscope slide; however, in doing so, they are destroyed in an uncontrollable way so that the obtained clumps that are more or less amorphous exhibit only minimal reactivity which is expressed in apparent volume changes as a reaction to changes of the calcium concentrations in the medium. To obtain and isolate forisomes from such plants and observe them in intact form was made possible only after many unsuccessful experiments and preliminary trials.

According to the invention it was finally found that it is beneficial to mechanically obtain the phloem as a starting material for isolating the forisomes in such a way that longitudinal sections of the stems or the like the donor plant is freed of the xylem and, subsequently, the phloem is separated from the cortex and the sclerenchyma. The cells of the phloem are then disintegrated and a suspension of the destroyed cells is filtered; the pores of the filter medium preferably have a size which prevents passage of intact cells. After isolation of the fraction containing the forisomes from the filtrate, they can be separated by means of gradient centrifugation from the other components.

For storing the obtained forisomes; a medium containing, for example, 70% saccharose or 70% glycerin in V medium (compositions see Example 1) (w/v) is suitable; the storability at −20 degrees Celsius is very high; at room temperature it is approximately three weeks.

The forisomes isolated in this way, and optionally stored, are completely intact. They have as a whole a significant reactivity. It was found that the "dispersed" state is visible and manipulatable in vitro as well as in the "crystalloid" state. The changes of the optical properties of the protein body upon conversion from "crystalloid" and "dispersed" conformation provides an independent proof for the occurring changes of the inner organization of the protein body.

As has been determined by means of the undamaged isolated protein bodies, the "dispersion" not only results in a thickening of the protein body in the directions perpendicular to its longitudinal axis but also a contraction along the longitudinal axis (see FIG. 1). Triggering of this conformational changes can be achieved by providing calcium ions with which the environmental concentration of these ions from less than approximately 30 nM Ca$^{++}$ can be raised (threshold concentration) to a value that is preferably significantly above this value. The reaction occurs without measurable time delay simultaneously with the change of the calcium concentration; it is complete, and a further increase of the calcium concentration does not affect any change. The thickening is reversible without limitation and practically can be repeated as often as desired (experimentally, at least 50 cycles were checked). The reversal of the conformation change is effected by lowering the calcium ion concentration in the environment of the forisomes to less than 30 nM, for example, by changing the medium or by adding chelating agents for the calcium. The contraction as a result of conformation change is up to approximately 30%; this is a remarkably high value in comparison to other actuator proteins. The conformation change takes place within the millisecond range.

The different reaction of completely intact "crystalloids" in comparison to the prior isolated damaged and amorphous clumps indicates that the capability for contraction requires substantially intact internal organization. However, this does not mean that only original "crystalloids" are able to react. Instead, the inventors could demonstrate that even sections which were obtained by smashing frozen protein bodies after thawing react in the "customary way". Portions of the "crystalloids" react thus often autonomously as long as the corresponding inner structure is present. According to the invention, it was determined that this reactivity, based on intact forisomes that are generally approximately 30-40 µm long and approximately 5-10 µm thick, at least up to a comminution in the range which is barely determinable by light optical microscopy, is maintained. This means that even forisome fragments with dimensions in the range of approximately 1 µm still exhibit the described behavior.

Calcium, similar to the in situ situation, can be functionally replaced by barium and strontium. Magnesium, however, remains without any effect in this connection.

Surprisingly, it was found that crystalline P-protein in vitro also reacts to changes of the pH value. When the pH value increases to above approximately 9.5, in particular, above 9.9, a reversible swelling of the protein body occurs. The reaction increases in a stepwise fashion with regard to its intensity up to a pH value of 10.6. When the pH value drops below a value of 9.5, the swelling disappears. There is no hysteresis. Above a pH value of 10.9 the forisomes will denature. The swelling induced by basic pH values causes, in contrast to the calcium ion addition, a contraction in the direction of the longitudinal axis of only a few percent so that in the end a volume increase can be observed. It thus differs from the conformation changes effected by cations. In the acidic range the P-proteins are irreversibly denatured at a pH value of approximately 4.5.

The forisomes of the present intention are comprised of two different proteins. This was determined by means of polyacrylamide gel electrophoresis of the protein material that had been isolated, as described above, by means of gradient centrifugation (see FIG. 3). The molecular weight of the two proteins that were found in this connection are in the range of approximately 55 to 65 kDa (P1) and 53 to 63 kDA (P2). The aforementioned polyacrylamide gel electrophoresis provides additional protein bands which can be correlated with additional proteins (P3 and P4) which, however, are decomposition products of P1 and P2. This hypothesis is supported by antibody studies. An enzymatic decomposition of the proteins P1 and P2 provides two peptides that have been analyzed by tandem mass spectroscopy (CID-MS/MS). These two peptides have the following structures.

```
                                          (seq. ID No. 1)
Leu-Gln-Asp-Asn-Pro-Gln-Glu-Val-Ile-Lys (first peptide).

(seq. ID No. 2)
Glu-Gly-Phe-Asp-Ile-Ala-Phe-Lys (second peptide).
```

In additional experiments it was also found that the protein P1 comprises the following amino acid sequence.

```
                                          (seq. ID No. 3)
    Glu-Val-Thr-Ser-Val.

(seq. ID No. 4)
    Val-Met-Glu-Val-Ser-Trp-His-Tyr-Lys-.

(seq. ID No. 5)
    Ala-Thr-Asp-Pro-.
```

According to the invention, forisomes or protein bodies have thus been found in the sieve tubes of the legume family that are comprised of at least two different proteins of comparable size and already in very small sized aggregates or complexes have reversible contracting properties that can be induced, on the one hand, by calcium ions or by other comparable bivalent ions and, on the other hand, also by a change of the pH value. It is remarkable in this connection that the pH value range in which the conformation change occurs is non-physiological and that the two observed conformation changes are different. No ATP as an energy provider is required for the initiation of the conformation change. With regard to contraction in the presence of calcium ions, the protein bodies are similar in certain ways to those of the spasmin of ciliates whose contraction is also calcium-dependent. However, spasmin contracts isotropic and reacts only at calcium concentrations that are 100 times higher.

As a result of the reactivity of very small protein bodies with a diameter of only approximately one micrometer or even less, it can be speculated that during the ontogenesis of the sieve elements in the beginning very small protein bodies with a correspondingly small diameter have condensed by addition of further subunits to the complex in the micrometer range that can be found today. This would explain why the protein bodies, despite variable size, are reactive in all states.

Bio-analog actuators are more and more of interest in bionics in the micro and nano ranges. With their mechanical activity, specific reactivity, longevity and obvious harmlessness for the human organism (the legume family members are important foodstuffs), the protein bodies of the present invention have properties as they are demanded for micro and nano actuators in particular in medical technology. In comparison to other contractile elements of the cyto-skeleton, they have the advantage that their structural coherence is not based on a continuous assembly and disassembly. Other motor proteins of the cyto-skeleton are subject to a continuous turnover which generally limits their longevity in vitro significantly.

The inventors were able to demonstrate that the contraction of the forisomes according to the invention can be converted in a quantifiable manner into force generation. The fact that forisomes pressed onto glass or other surfaces adhere thereto enables, for example, the fixation of individual specimens between two spring arms, for example, made of glass fibers. The adhesive properties of the forisomes on the spring arms can be improved, as needed, by a suitable coating of the material of the spring arms, for example, with poly-L-lysine or adhesives such as, for example, Kwik-Sil (trade name of World Precision Instruments, Sarasota, Fla., U.S.A.). When, by adding calcium ions, the contraction is triggered, each individual protein body produces such a great mechanical force that the spring arms are significantly bent.

Such an arrangement is therefore suitable for micro tweezers for manipulating and positioning organic or inorganic structures such as cells, tissue, or molecular bodies. In FIG. 4, such tweezers are schematically illustrated: 4A illustrates the open state with relaxed forisome, 4B illustrates the closed state with contracted forisome. The movement of the tweezers can be controlled manually under the light optical microscope or electronically. Since the size of the functioning forisomes is in the range of 1 µm (or even less than that) up to 40 µm, the opening width of the tweezers tip can be adjusted within the corresponding range. With such tweezers, smallest bodies or substance amounts can be transported in a targeted way and reacted and biological processes can be precisely initiated at the desired location. As an alternative, the forisomes can be used, for example, as sensor elements for a pH change in the range of approximately 9.5 to 10 and for the increase of calcium ion concentrations in a medium from below to above 30 nM or vice versa and are simultaneously useable as indicator elements: Forisomes can be arranged between two spring arms such that their contraction under the aforementioned conditions of the surrounding medium effect a contact of the tips of these spring arms. When the tips are electrically conducting, an electrical circuit is closed via these spring arms upon contact of the tips, and the change of the hydrogen or calcium ion concentration in the medium, for example, in an enzymatic process, can be directly detected. Such an element is schematically illustrated in FIG. 5: 5A indicates the open electrical circuit with relaxed forisome, 5B shows the closed electrical circuit with contracted forisome.

BRIEF DESCRIPTION OF DRAWINGS

FIG. 1A shows a forisome according to the invention in the relaxed state.

FIG. 1B shows the forisome according to the invention in the contracted state.

FIG. 2 shows for illustration purposes schematically the phloem of higher plants comprising a system of microtubules (sieve elements) serving for transporting photo assimilate.

Figure 4A:
FIG. 4A shows schematically tweezers in the open state with relaxed forisome.
Figure 4B:

4B illustrates the closed state of the tweezers of FIG. 4A with contracted forisome.

Figure 5A:
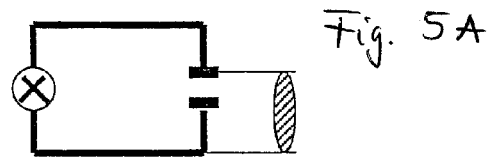

FIG. 5A shows schematically an open electrical circuit with relaxed forisome.

Figure 5B:
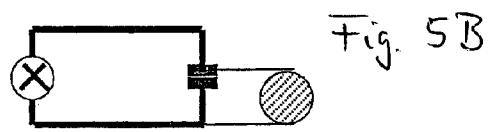

FIG. 5B shows the electrical circuit of FIG. 5A in the closed state with the contracted forisome.

Figure 6A:
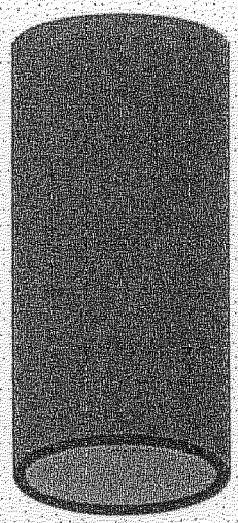

FIG. 6A shows schematically an intact stem before separating the phloem for isolating the forisomes.

Figure 6B:
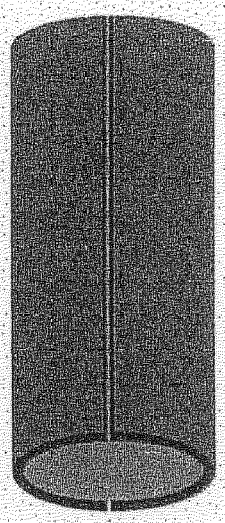

FIG. 6B illustrates an effective technique for isolating the phloem by carrying out two oppositely positioned cuts along the longitudinal axis of the plant, wherein the cuts cut through the bark to the xylem of the conducting tissue.

Figure 6C:
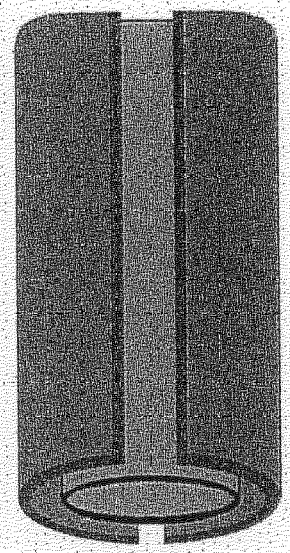

FIG. 6C shows the removal of the bark from the xylem.

Figure 6D:
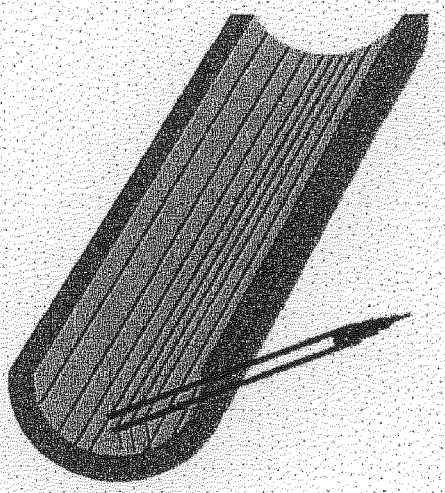

FIG. 6D illustrates removal of the sclerenchyma fibers by means of tweezers from the cortex together with the phloem that adheres to the fibers.

Figures 7A, 7B:
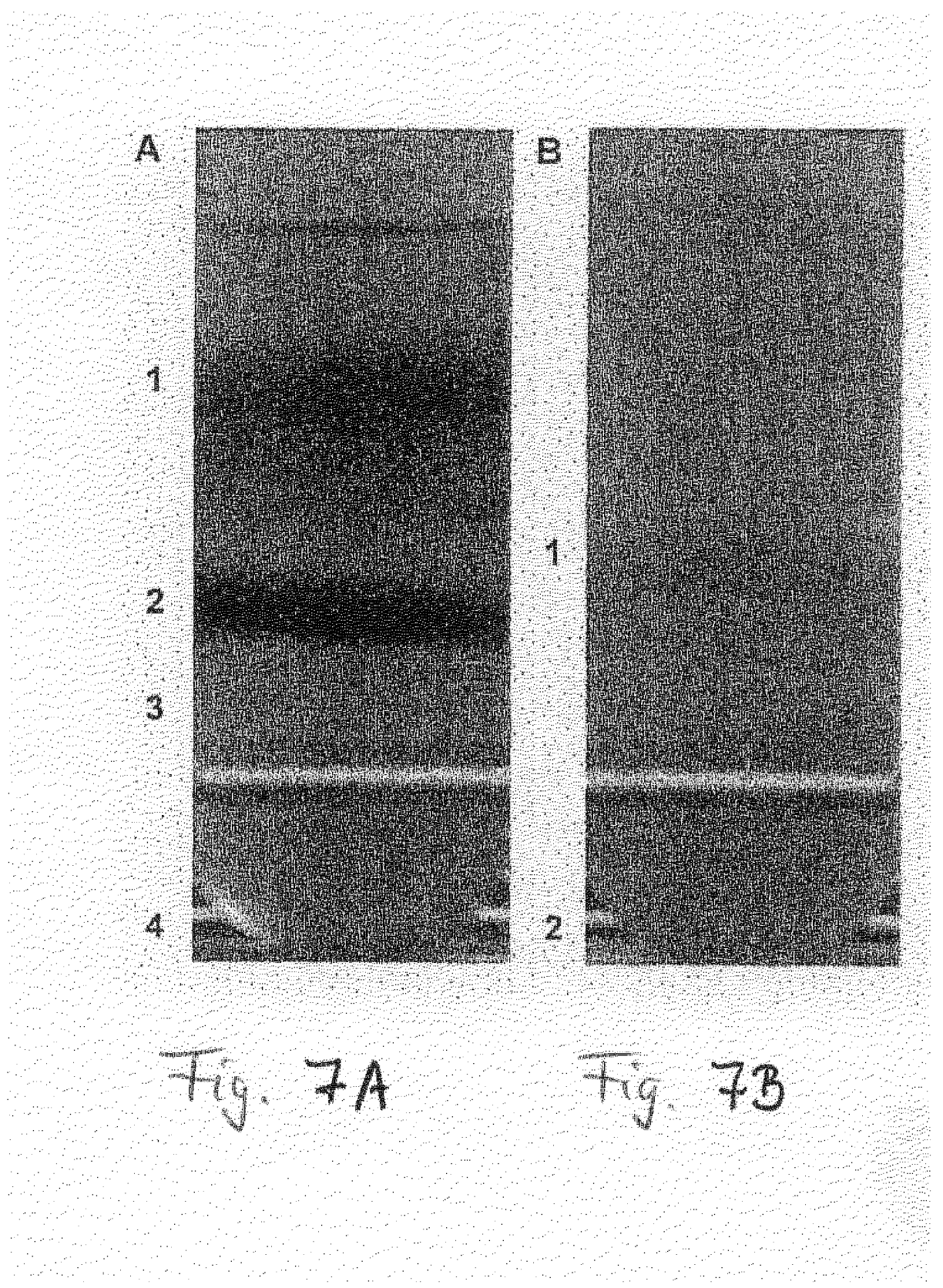

FIG. 7A shows the band pattern obtained by centrifugation according to the example 1A.

FIG. 7B shows the band pattern obtained by centrifugation according to the example 1B.

Figure 8:
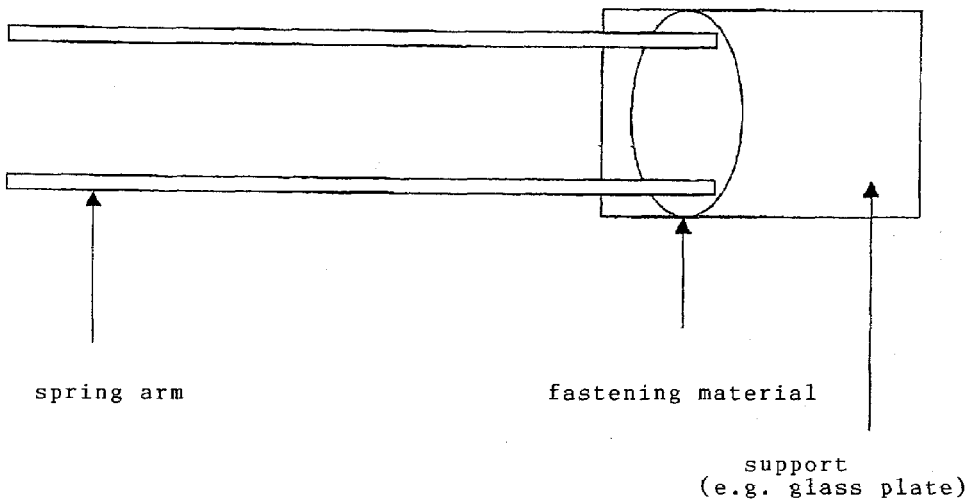

FIG. 8 shows a tweezers arrangement with spring arms fastened on a support at a spacing to one another that corresponds to the length of the forisome.

Figure 9A:
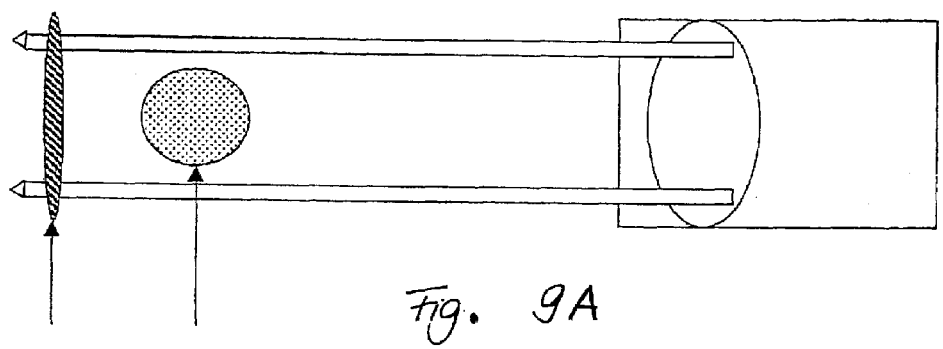

FIG. 9A shows the tweezers of FIG. 8 in the open state with the forisome in the relaxed state.

Figure 9B:
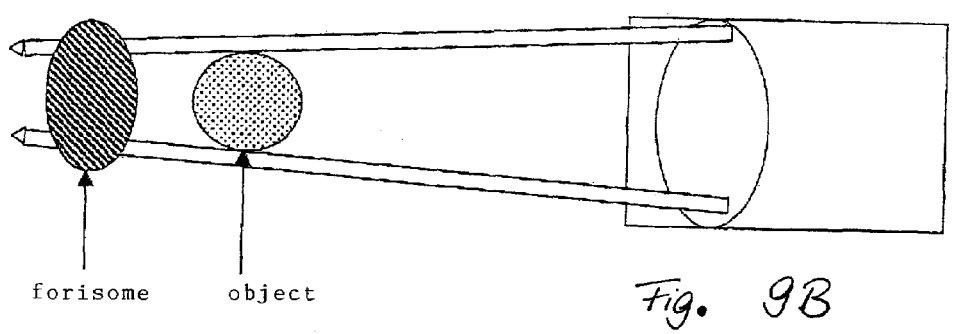

FIG. 9B shows the tweezers of FIG. 8 in the closed state with the forisome in the contracted state so that the object is secured between the spring arms.

Figure 10A:
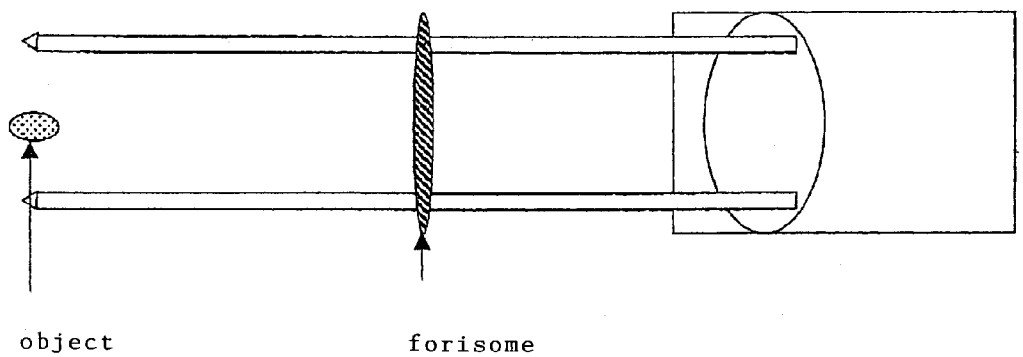

FIG. 10A shows a tweezers arrangement similar to FIG. 9A where the forisome is located closer to the support and the tips of the spring arms are designed to grip an object.

Figure 10B:
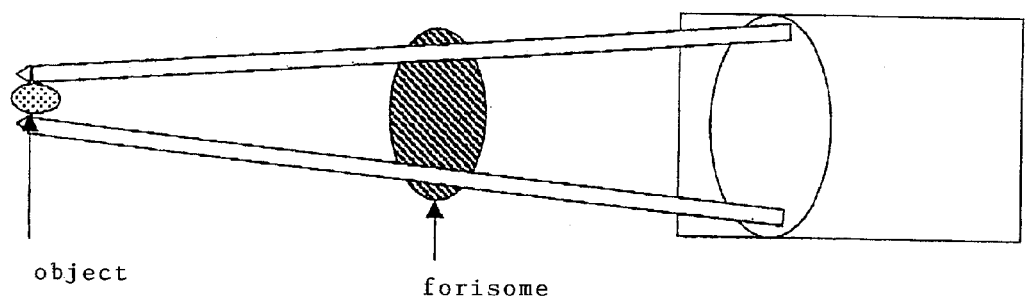

FIG. 10B shows the tweezers of FIG. 10A in the closed state with the forisome in the contracted state so that the object is secured between the tips of the spring arms.

Figure 11:
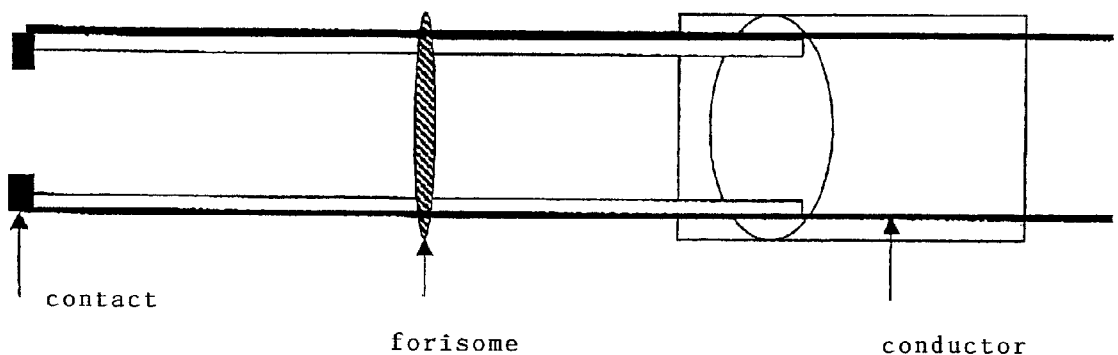
Figure 11:
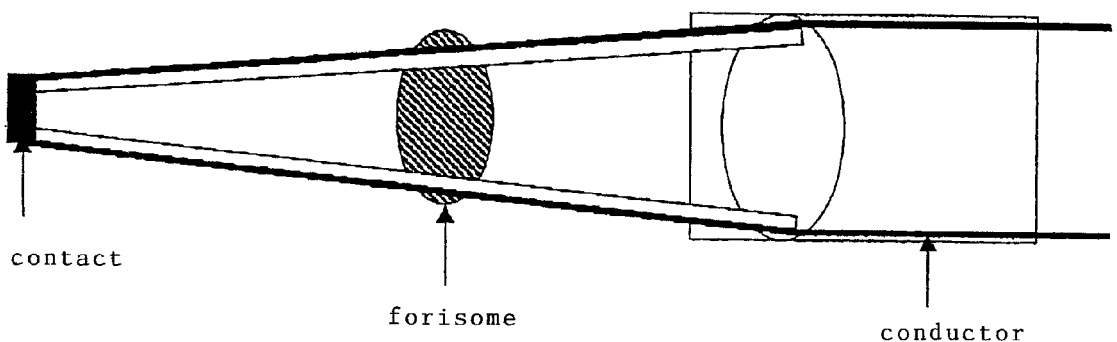

FIG. 11A shows an electric circuit arrangement 9A with contacts between which a forisome is located; the forisome is relaxed and the circuit is open.

FIG. 11B shows the circuit of FIG. 11A in the closed state with the forisome in the contracted state pulling the contacts against one another so that electric current can flow.

DETAILED DESCRIPTION

In the following the invention will be explained in more detail with the aid of preliminary as well as comparative examples.

EXAMPLE 1

Purification of Forisomes of *Vicia faba*

Remarks: *Vicia faba* L. cv *Witkiem major* (Nunhem Zadenh BV, Haelen, The Netherlands) or other *Vicia faba* varieties can be grown without problems in a greenhouse.

1. Separation of the root from the shoot at the hypocotyl: the stem of the plants (7-8 weeks old) were separated by a razor blade shortly above the soil line; subsequently, all leaves were removed, and 10 cm of the stem tip cut off.

2. Separation of the cortex inclusive phloem from the xylem cylinder: method for separation of the phloem from the rest of the stem (the intact stem is illustrated in FIG. 6A). An effective technique was found in carrying out two oppositely positioned cuts along the longitudinal axis of the plant that cut through the bark to the xylem of the conducting tissues which are annularly arranged (see FIG. 6B). Subsequently, the bark was carefully removed along the xylem (FIG. 6 C.). It was observed when doing so that the phloem adhered to the inner side of the removed bark and, in this way, could be cleanly removed from the xylem. Special attention had to be directed to the area of the nodes because here the conducting tissue branches off, and a clean separation is therefore difficult to obtain at these locations. Subsequently, the inner xylem cylinder could be disposed of. *Vicia* plants in which the secondary growth had not yet begun showed an annular distribution of the sclerenchyma fibers in the cortex upon which the phloem was supported. As a result of the strength of these fibers, they could be easily removed by means of tweezers from the cortex (FIG. 6D); the phloem adhered to them.

3. Placement of the cortex into V medium (10 mM EDTA, 10 mM Tris, 100 mM KCl, pH 7.3): a prior incubation for one hour in the V medium facilitated the separation of phloem and sclerenchyma (step 4) and enabled also a regeneration of the forisomes into the crystalline form.

4. Separation of the phloem from the sclerenchyma and cortex: the phloem, after termination of the incubation period, was separated by means of a blunt scalpel from the inner surface of the bark.

5. Pestling the phloem under liquid nitrogen (intermittent sieving is advantageous in order to protect already released forisomes from destruction): the phloem was dried with cellulose and was then pestled in a mortar under liquid nitrogen for approximately 10 minutes up to the point of achieving a powder-like state and was then taken up in V medium. The suspension was then filtered through a tissue sieve and the remaining residue was then thoroughly rinsed several times with 5 ml V medium. The pore size of the tissue sieve was varied and the sizes 100 µm, 80 µm, and 59 µm were tested. The pore size of 59 µm was found to be optimal because the forisomes with a length of approximately 30 µm could fall through without problems even when adhering to other small size material. Moreover, this pore size prevents passage of cells that have not yet been destroyed.

6. The filtrate of step 5 with the forisomes contained therein was centrifuged at 5000×g at 4 degrees Celsius for 10 minutes. The supernatant was disposed of.

7. The pellet resulting from centrifugation was redissolved in 5 ml V medium and applied onto a Nycodenz gradient (80-20% in V medium): For preparation of gradient centrifugation by means of gradient pouring device a continuous gradient was poured. For this purpose, a column was filled with 15 ml 80% Nycodenz solution while the other column was filled with 3.75 ml 80% Nycodenz solution and with 11.25 ml plant suspension—corresponding to a 20% Nycodenz solution. By means of the gradient pouring device a gradient of 80% at the bottom up to 20% at the upper edge of the centrifuge tube could be obtained.

8. The Nycodenz gradient according to step 7 was centrifuged for three hours at 150,000×g in an ultra centrifuge. By means of this centrifugation a band pattern as illustrated in FIG. 7A was obtained. The reference numeral 1 indicates a band of chloroplasts as the uppermost layer. In the middle area identified by reference numeral 2 a wide, relatively sharply discernable band is present which is comprised of membrane residues. At the bottom of the centrifuge tube, identified at 4, a pellet of cell wall debris is found. Approximately at the upper third of the phase between the membrane band and the cell wall pellet a thin band can be identified which is comprised exclusively of forisomes (identified in FIG. 7A by reference numeral 3).

9. To the removed fraction (forisome-containing) twice the amount of liquid volume was added and the mixture centrifuged at 5,000×g for 10 minutes. The supernatant was disposed of.

10. For storing, the forisomes were frozen with 70% saccharose in V medium (w/v) at −20 degrees Celsius.

Nycodenz has the following formula.

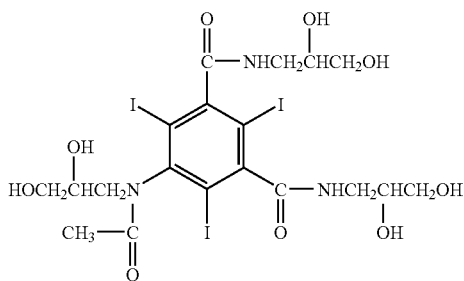

The compound is used as a non-ionic density gradient medium. Reference: Rickwood, D., et al. Anal. Biochem., 123 23 (1982). Beilstein Registry No. 2406632.

Available through Nycomed Pharma AS, Norway.

Synonym: Histodenz (available from Sigma-Aldrich).

EXAMPLE 1A

Example 1 was repeated with Vicia plants of the same age whose secondary growth had already started. The separation of cortex and phloem from the xylem cylinder was carried out as follows.

In these plants, the phloem closed to form a cylinder by formation of an interfascicular cambium. The sclerenchyma fibers were also formed stronger so that, after separation of the cortex from xylem, a removal of the sclerenchyma fibers by means of tweezers was difficult to perform and resulted in a high loss of phloem. In these plans, it was much more effective to remove the phloem after termination of the incubation period by means of a blunt scalpel from the inner surface of the bark. This has the advantage that also the sclerenchyma fibers can be separated. Moreover, the yield of phloem is significantly higher than in the Vicia plants without secondary growth.

EXAMPLE 1B

Example 1 was repeated wherein the gradient centrifugation according to steps 7 and 8 was carried out with a plant suspension to which was added, before pouring the gradient, 0.1% Triton X100 in order to remove membrane and cell wall proteins and to reduce possibly occurring interactions between the forisomes and the membrane residues. After centrifugation under the same conditions, a band distribution according to FIG. 7B was obtained. Even though no chloroplast band could be observed, the forisomes, despite the treatment with Triton, were found primarily within the membrane band (1).

EXAMPLE 2

Separation of Forisomes by Means of SDS Polyacrylamide Gel Electrophoresis

Figure 3:
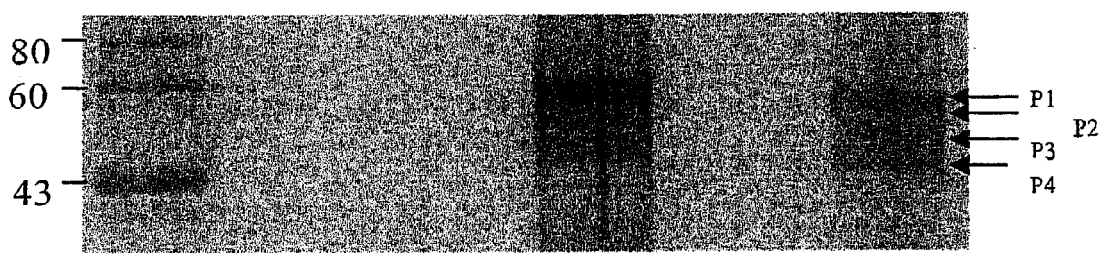
FIG. 3 shows a gel with forisome components separated by electrophoresis.

1. The forisomes were centrifuged in V medium for 10 minutes at 5,000×g.
2. The supernatant was disposed of and the forisomes were taken up in 250 μl 50 mM Tris-HCl buffer pH 6.8.
3. To the forisome solution was added 200 μl 10% sodium dodecyl sulfate solution, 25 μl 60% saccharose solution, and 2.5 μl 2-mercapto ethanol, and the forisome solution was denatured for 5 minutes at 95 degrees Celsius.
4. The mixture was centrifuged for 5 minutes at 12,000×g.
5. The denatured proteins are separated by means of 10% SDS polyacrylamide gel according to Laemmli (1970) by electrophoresis.
6. The proteins were made visible subsequently by Coomassie staining. FIG. 3 shows the gel with the separated forisome components. The molecular weight is provided in kDa.

EXAMPLE 3

Determination of the Peptide Sequences by Means of Mass Spectroscopy

1. Enzymatic Digestion with Trypsin.

The protein bands of the SDS PAGE according to Example 2 were cut from the gel and placed into an Eppendorf vessel. After dehydration of the gel pieces by means of acetonitrile, the acetonitrile is removed. Subsequently, the gel pieces were dried in a vacuum centrifuge. Subsequently, 10 mM dithiotreitol (DTT) in 100 mM $NH_4HCO_3$ were added until all gel pieces are covered completely with the solution. The proteins were reduced for one hour at 56 degrees Celsius. After cooling to room temperature, the DTT solution is replaced by the same volume of 55 mM iodoacetamide in 100 mM $NH_4HCO_3$. After 45 minutes incubation at room temperature in darkness, the gel pieces are washed with 50-100 μl 100 mM $NH_4HCO_3$ for 10 minutes, dried with acetonitrile, rehydrogenated with 100 mM $NH_4HCO_3$ and again dried with the same volume of acetonitrile. The liquid phase was removed and the gel pieces were dried completely in a vacuum centrifuge. Subsequently, to the gel pieces a "digestion buffer" (50 mM $NH_4HCO_3$, 50 mM $CaCl_2$, and 12.5 ng/μl trypsin) was added at 0 degrees Celsius. After 45 minutes, the supernatant was removed and replaced with 5-10 μl of a buffer comprised of 50 mM $NH_4HCO_3$ and 5 mM $CaCl_2$ in order to keep the gel pieces moist during digestion for 12 hours at 37 degrees Celsius. Subsequently, the resulting peptides are extracted with 20 mM $NH_4HCO_3$ and three-fold extraction with a mixture of 5% formic acid, 45% desalinated water, and 50% acetonitrile (each time for 20 minutes) at room temperature, and the combined extracts are dried completely in a vacuum centrifuge.

2. Desalination of the Samples.

The sample was taken up in 10 μl % TFA and subsequently desalinated with ZipTips™ (registered trademark of the Millipore Corporation, Bedford, Mass., USA or a subsidiary).

First the equilibration of the tip with 10 μl of a mixture of 50% water (HPLC grade) and 50% acetonitrile (HPLC grade) and, subsequently, removal were carried out. This process was repeated once. The tip is then moistened with 10 μl 0.1% trifluoroacetic acid solution in that this solution is sucked in and released twice.

The peptide mixture from digestion with trypsin is now completely sucked in and then again released. This process is repeated nine times.

The bonded peptides are then freed from salt by washing 10 times with 0.1% trifluoroacetic acid solution. Subsequently, the peptides are eluted with 3-10 μl of a mixture of 0.1% formic acid, 39.9% water (HPLC grade), and 60% acetonitrile (HPLC grade). The eluted solution is then again sucked in and released four times.

3 μl of the eluted solution are filled into an nanospray glass capillary. The glass capillary is fastened in a holder provided for this purpose and the holder is transferred into the nanospray ion source.

Calibration of the mass spectrometer is realized for a mass spectrum with a peptide mixture (1 μmol/l each of angiotensin I, substance P, Glufibrinopeptide, renin substrate, ACTH clip 18-39, and bovine insulin) and for MS/MS mode with the Glufibrinopeptide (100 nmol/).

3. Recording the Mass Spectra or the CID-MS/MS Spectra.

All mass spectra and MS/MS are recorded with a Q-TOF-2™ (trademark of the company Micromass). For controlling the mass spectrometer and data processing the software programs Masslynx 3.5™ and ProteinLynx 1.0™ are used.

The capillary voltage is between 1.0-1.5 kV, the cone voltage is varied within the mass range m/z 400-2,500 from 10 eV to 100 eV.

Argon pressure in the collision cell is 10–6 mbar for CID-MS/MS (5+1). The recording time is for each scan 2.4 seconds with an interval of 0.1 seconds between each scan.

For de novo sequencing all formed peptide ions of the enzymatically digested protein are selected individually and completely automatically by means of the "collision induced dissociation" (CID) and fragmented (CID-MS/MS). In this context, exclusively 2-, 3-, and 4-protonated species are selected. Based on the obtained MS/MS spectra sets, sequence information of the corresponding peptides are determined with software support. This sequence information is compared by means of a "blast" search in the Mascot data base in order to find homolog proteins. All MS/MS spectra and the resulting amino acid sequences of the corresponding peptides are evaluated.

EXAMPLE 4

Induction of Contraction of Forisomes by Calcium Ion Addition

Isolated forisomes are transferred into a test chamber of a volume of 1 mL. In this connection, an isolated forisome is pressed by means of a micro injection needle with one end onto the chamber bottom, respectively, in order to prevent drifting when flushing the chamber. Subsequently, by means of an automatic flow-through device alternatingly V medium (10 mM EDTA, 10 mM TRIS pH 7.3, 100 mM KCl) and calcium medium (19 mM $CaCl_2$, 10 mM TRIS-HCl pH 7.3, 100 mM KCl) are applied to the forisome, which results in a conformation change, respectively. The conformation change can be observed microscopically by means of a camera that is mounted on the observing microscope. In FIGS. 1A and 1B the two conformations that the forisome has in the V medium, i.e., in the relaxed state (FIG. 1A), and in the Ca medium, i.e., in the contracted state (FIG. 1B), are illustrated. The microscope was within the direct light interference contrast mode for recording the images. The width of the sections corresponds to 30 μm each.

EXAMPLE 5

Induction of Volume Enlargement of Forisomes by Increasing the pH Value

An isolated forisome is introduced into a test chamber having a volume of 1 ml in which V medium is contained. An isolated forisome is pressed by means of a micro injection needle with one end onto the chamber bottom in order to prevent drifting during flushing of the chamber. Subsequently, starting at a pH value of 7.3, the pH value is increased by means of automatic flow-through devices in steps of 0.3 units; the employed medium is free of calcium. A first reaction of the forisome can be detected at a pH value of 9.4. The intensity of the reaction increases with increasing pH value up to pH 10.6. The reaction is completely reversible after introducing V medium of pH 7. Starting at and above a pH value of 10.9 the forisome becomes denatured.

When instead of EDTA/TRIS other buffer media are used that have chelating properties relative to calcium ions, the same reaction course is observed.

In the acidic range, the structure of the forisome will change upon reaching a pH value of 4.9. However, there is no step-wise increase of the reaction. Already at a pH value of 4.6 the forisome is irreversibly denatured.

The confirmation change can be observed microscopically by means of a camera which is mounted on the observing microscope.

EXAMPLE 6

Manufacturing Micro or Nano Tweezers for Manipulation of Individual Cells or Molecules In FIG. 8, a tweezers arrangement is illustrated in which two spring arms (for example, fiberglass or micro pipettes) are positioned and fastened on a support (for example, by means of an adhesive) at a spacing to one another corresponding to the length of the forisome. Accordingly, the forisome can be penetrated at its ends by means of the tips of the spring arms (see FIG. 9A). In the case of fiberglass arms, the tips which are produced naturally during the production process are used. In the case of other materials, the tips can be produced, for example, by etching. The tweezers are then moved into the vicinity of the object to be gripped so that the object comes to rest between the spring arms in the vicinity of the forisome (see FIG. 9A). As an alternative, the forisome can be attached by adhesion on a central location on the spring arms, wherein the spring arms can be coated so as to have increased adhesion should the adhesion of the forisome on the spring arms be insufficient. In this way, glass surfaces can be coated, for example, with poly-L-lysine or comparable materials. By means of the central positioning of the forisome, an increased spring travel of the arms is obtained in this method (see FIG. 10A).

Depending on the material of the spring arms and the different spring constants, their diameter, their length, or the position and/or size of the forisome must be adjusted. In this example, the spring arms are made of borosilicate glass with a diameter of approximately 1-2 µm and a length of approximately 100-500 µm.

The control of the forisome can be achieved in different ways depending on the application. By adding free $Ca^{++}$ to the solution or by pH value changes, a contraction or a volume increase can be triggered. The media for this purpose can be, for example, those mentioned in examples 4 and 5. The contraction by adding $Ca^{++}$ effects closure of the tweezers, as illustrated in FIGS. 9B and 10B.

EXAMPLE 7

Micro or Nano Switches for Detecting pH Value and Calcium Ion Concentration Changes in a Medium In a similar way as in example 6 for tweezers, micro or nano switches can be constructed which are suitable as sensors for indicating a pH value change or change of calcium iron concentrations in the range in which the reversible conformation change of the forisomes takes place. For this purpose, the spring arms are made of corresponding metals, of glass coated with a conducting material or electrodes are mounted on the tips (see FIG. 11A). The conformation changes of the forisomes caused by a corresponding change of the pH value or of the calcium ion concentration in the medium surrounding the forisome moves the contacts together (or opens them) and this results in a noticeable decrease (or increase) of the resistance within the electric circuit; this can be detected with conventional means as a switching step and tapped (see FIG. 11B) The contacts are ideally silver electrodes or copper electrodes (depending on the solution). For special fields of application contacts made of other materials are also possible.

While specific embodiments of the invention have been shown and described in detail to illustrate the inventive principles, it will be understood that the invention may be embodied otherwise without departing from such principles.

What is claimed is:

1. A protein crystalloid body (forisome) isolated from Fabaceae, wherein the protein crystalloid body has a reversible, anisotropic contractability such that:

the protein crystalloid body becomes thicker in a direction perpendicular to a longitudinal axis of the protein crystalloid body and shorter along said longitudinal axis when increasing a calcium ion concentration in a medium surrounding the protein crystalloid body past a threshold value of approximately 30 nM and the protein crystalloid body becomes thinner in said perpendicular direction and longer along said longitudinal axis when decreasing the calcium ion concentration below the threshold value of approximately 30 nM; and the protein crystalloid body becomes thicker in said perpendicular direction when increasing a pH value of a medium surrounding the protein crystalloid body to a value above approximately 9.5 without becoming shorter along said longitudinal axis and the protein crystalloid becomes thinner in said perpendicular direction without becoming longer along said longitudinal axis when decreasing the pH value below approximately 9.5;

wherein the protein crystalloid body comprises a first protein and a second protein; and wherein, when digesting the first and second proteins by trypsin, a peptide (seq. ID No. 2)
Glu-Gly-Phe-Asp-Ile-Ala-Phe-Lys is found.

2. The protein crystalloid body according to claim 1, wherein the first protein has a molecular weight in the range of approximately 55-65 kDa and the second protein has a molecular weight in the range of 53-63 kDa.

3. A protein crystalloid body (forisome) isolated from Fabaceae, wherein the protein crystalloid body has a reversible, anisotropic contractability such that:

the protein crystalloid body becomes thicker in a direction perpendicular to a longitudinal axis of the protein crystalloid body and shorter along said longitudinal axis when increasing a calcium ion concentration in a medium surrounding the protein crystalloid body past a threshold value of approximately 30 nM and the protein crystalloid body becomes thinner in said perpendicular direction and longer along said longitudinal axis when decreasing the calcium ion concentration below the threshold value of approximately 30 nM; and the protein crystalloid body becomes thicker in said perpendicular direction when increasing a pH value of a medium surrounding the protein crystalloid body to a value above approximately 9.5 without becoming shorter along said longitudinal axis and the protein crystalloid becomes thinner in said perpendicular direction without becoming longer along said longitudinal axis when decreasing the pH value below approximately 9.5;

wherein the protein crystalloid body comprises a first protein and a second protein;

wherein, when digesting the first and second proteins by trypsin, a peptide Glu-Gly-Phe-Asp-Ile-Ala-Phe-Lys (seq. ID No. 2) is found;

wherein the first protein has a molecular weight in the range of approximately 55-65 kDa and the second protein has a molecular weight in the range of 53-63 kDa;

wherein, when digesting the first and second proteins by trypsin, a further peptide Leu-Gln-Asp-Asn-Pro-Gln-Glu-Val-Ile-Lys (seq. ID No. 1) is found; and wherein the first protein further contains the fragments:

(seq. ID No. 3)
Glu-Val-Thr-Ser-Val;

(seq. ID No. 4)
Val-Met-Glu-Val-Ser-Trp-His-Tyr-Lys-;

(seq. ID No. 5)
Ala-Thr-Asp-Pro-.

4. The protein crystalloid body according to claim 1, having a length of approximately 1 μm to approximately 40 μm and a diameter perpendicularly to the length of approximately 1 μm to approximately 10 μm.

5. The protein crystalloid body according to claim 4, wherein the first protein has a molecular weight in the range of approximately 55-65 kDa and the second protein has a molecular weight in the range of 53-63 kDa.

6. The protein crystalloid body according to claim 5, wherein, when digesting the first and second proteins by trypsin, a further peptide

```
                                              (seq. ID No. 1)
    Leu-Gln-Asp-Asn-Pro-Gln-Glu-Val-Ile-Lys
``` is found;
and wherein the first protein further contains the fragments:

```
                                              (seq. ID No. 3)
    Glu-Val-Thr-Ser-Val;

(seq. ID No. 4)
    Val-Met-Glu-Val-Ser-Trp-His-Tyr-Lys-;

(seq. ID No. 5)
    Ala-Thr-Asp-Pro-.
```

7. The protein crystalloid body according to claim 1, wherein the contractibility along the longitudinal axis is up to approximately 30% accompanied by an expansion perpendicular to the longitudinal axis of up to approximately 100%.

8. A method for isolating protein crystalloid bodies of claim 1, wherein the method comprises the steps of:
A) obtaining phloem of a plant of the family Fabaceae;
B) destroying the cells of the phloem;
C) preparing a suspension of the destroyed cells of step B);
D) filtering the suspension;
E) separating the protein crystalloid bodies from other components of the suspension by gradient centrifugation.

9. The method according to claim 8, wherein in the step D) a Nycodenz solution is used for gradient centrifugation, wherein in the step C) the suspension contains a medium containing KCl in a suitable buffer.

10. The method according to claim 8, wherein the plant is selected from the family of Vicia faba.

11. A method of operating micro tweezers, comprising the steps of:
connecting at least one protein crystalloid body of claim 1 to two opposed spring arms of micro tweezers;
increasing a concentration of calcium ions in a medium surrounding the at least one protein crystalloid body from a value significantly below 30 nM to a value significantly above 30 nM.

12. A method for operating a display element for a change of a calcium ion concentration from significantly below 30 nM to significantly above 30 nM or for change of the pH value from below pH 9.4 to pH 10.0 in a medium, the method comprising the steps of:
connecting a protein crystalloid body of claim 1 having a suitable size to two opposed spring arms having tips that upon contraction of the protein crystalloid body contact one another, wherein the spring arms and the tips are configured such that when the tips contact one another an electric circuit is closed and electric current flows in the electric circuit;
using the electric current flow or interruption of the electric circuit as a signal for indicating that the calcium ion concentration has increased to a value significantly above 30 nM or has dropped to a value significantly below 30 nM or that the pH value has risen above pH 10.0 or dropped below pH 9.4.

\* \* \* \* \*

```
                         SEQUENCE LISTING

<160> NUMBER OF SEQ ID NOS: 5

<210> SEQ ID NO 1
<211> LENGTH: 10
<212> TYPE: PRT
<213> ORGANISM: Vicia faba
<220> FEATURE:
<221> NAME/KEY: PEPTIDE
<222> LOCATION: (1)..(10)
<223> OTHER INFORMATION:

<400> SEQUENCE: 1

Leu Gln Asp Asn Pro Gln Glu Val Ile Lys
1               5                   10

<210> SEQ ID NO 2
<211> LENGTH: 8
<212> TYPE: PRT
<213> ORGANISM: Vicia faba
<220> FEATURE:
<221> NAME/KEY: PEPTIDE
<222> LOCATION: (1)..(8)
<223> OTHER INFORMATION:

<400> SEQUENCE: 2

Glu Gly Phe Asp Ile Ala Phe Lys
1               5

<210> SEQ ID NO 3
<211> LENGTH: 5
<212> TYPE: PRT
<213> ORGANISM: Vicia faba
<220> FEATURE:
<221> NAME/KEY: PEPTIDE
<222> LOCATION: (1)..(5)
<223> OTHER INFORMATION:

<400> SEQUENCE: 3

Glu Val Thr Ser Val
```

-continued

```
<210> SEQ ID NO 4
<211> LENGTH: 9
<212> TYPE: PRT
<213> ORGANISM: Vicia faba
<220> FEATURE:
<221> NAME/KEY: PEPTIDE
<222> LOCATION: (1)..(9)
<223> OTHER INFORMATION:

<400> SEQUENCE: 4

Val Met Glu Val Ser Trp His Tyr Lys
1               5

<210> SEQ ID NO 5
<211> LENGTH: 4
<212> TYPE: PRT
<213> ORGANISM: Vicia faba
<220> FEATURE:
<221> NAME/KEY: PEPTIDE
<222> LOCATION: (1)..(4)
<223> OTHER INFORMATION:

<400> SEQUENCE: 5

Ala Thr Asp Pro
1
```